United States Patent
Meyer et al.

[11] 3,981,882
[45] Sept. 21, 1976

[54] PROCESS FOR PREPARING 4-ARYL OF HETERO-6-AMINO-3,4-DIHYDROPYRID-2-ONE-3,5-DICARBOXYLIC ACID ESTER

[75] Inventors: Horst Meyer; Friedrich Bossert, both of Wuppertal; Wulf Vater, Opladen; Kurt Stoepel, Wuppertal, all of Germany

[73] Assignee: Bayer Aktiengesellschaft, Germany

[22] Filed: July 16, 1975

[21] Appl. No.: 596,507

Related U.S. Application Data

[62] Division of Ser. No. 531,999, Dec. 12, 1974, which is a division of Ser. No. 390,193, Aug. 21, 1973, Pat. No. 3,925,395.

[30] Foreign Application Priority Data

Aug. 31, 1972 Germany............................ 2242787

[52] U.S. Cl............... 260/295.5 R; 260/256.4 R; 260/256.4 C; 260/287 R; 260/294.8 D; 260/294.8 G; 260/294.8 F; 260/294.9; 260/295.5 B; 424/266
[51] Int. Cl.²....................................... C07D 213/55
[58] Field of Search............... 260/287 R, 256.4 R, 260/256.4 C, 294.8 D, 294.8 F, 294.8 G, 295.5 R, 294.9, 295.5 B

[56] References Cited
UNITED STATES PATENTS
3,923,818  12/1975  Bossert et al. .............. 260/295.5 R Primary Examiner—Alan L. Rotman

[57] ABSTRACT

3,4-Dihydropyridones of the formula

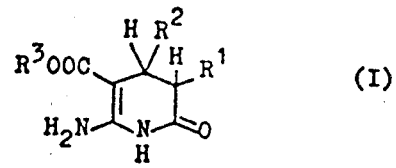

wherein $R^1$ is hydrogen, straight or branched chain alkyl, or —COOR' wherein R' is a straight, branched or cyclic, saturated or unsaturated hydrocarbon or said hydrocarbon interrupted by 1 or 2 oxygen atoms; $R^2$ is a straight, branched or cyclic, saturated or unsaturated hydrocarbon, aryl unsubstituted or substituted by 1 to 3 of the same or different substituents selected from the group consisting of alkyl, alkoxy, halogen, nitro, cyano, trifluoromethyl, carbalkoxy, and $SO_n$-alkyl wherein $n$ is 0, 1 or 2, or naphthyl, quinolyl, isoquinolyl, pyridyl, pyrimidyl, thenyl, furyl or pyrryl unsubstituted or substituted by 1 or more substituents selected from the group consisting of alkyl, alkoxy and halogen; and $R^3$ is a straight or branched chain hydrocarbon or said hydrocarbon interrupted by 1 or 2 oxygen atoms, are produced by reacting an α,β-unsaturated carboxylic acid ester of the formula

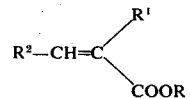

wherein R is alkyl, alkenyl or alkynyl, and $R^1$ and $R^2$ are as above defined, with an amidine of the formula

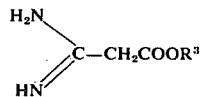

wherein $R^3$ is as above defined. These compounds are useful as coronary agents and as anti-hypertensive agents.

6 Claims, No Drawings

PROCESS FOR PREPARING 4-ARYL OF HETERO-6-AMINO-3,4-DIHYDROPYRID-2-ONE-3,5-DICARBOXYLIC ACID ESTER

This is a division of Ser. No. 531,999, filed Dec. 12, 1974, which is a division of Ser. No. 390,193, filed Aug. 21, 1973, now U.S. Pat. No. 3,925,395, issued Dec. 9, 1975.

The present invention is concerned with 3,4-dihydropyridones, a process for their production, pharmaceutical compositions embodying said compounds as the active agent and the use of said compounds as coronary dilating agents and as anti-hypertensive agents.

It has already been disclosed that the reaction of benzylidenemalonic acid diethyl ester with β-aminocrotonic acid ethyl ester yields a 3,4-dihydropyridone derivative (compare Knoevenagel, Fries, Ber. 31, 761 (1898)).

More particularly, the present invention is concerned with 3,4-dihydropyridones of the formula

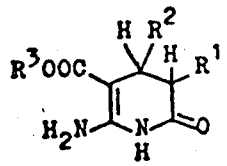
(I)

wherein $R^1$ is hydrogen, straight or branched chain alkyl, especially lower alkyl, or —COOR' wherein R' is a straight, branched or cyclic, saturated or unsaturated hydrocarbon, especially lower alkyl, lower alkenyl, lower alkynyl, cycloalkyl of 3 to 7 carbon atoms or cycloalkenyl of 3 to 7 carbon atoms, or said hydrocarbon interrupted by 1 or 2 oxygen atoms, especially lower alkyl, lower alkenyl, lower alkynyl, cycloalkyl of 3 to 7 carbon atoms or cycloalkenyl of 3 to 7 carbon atoms interrupted by 1 or 2 oxygen atoms; $R^2$ is a straight, branched or cyclic, saturated or unsaturated hydrocarbon, especially lower alkyl, lower alkenyl, lower alkynyl, cycloalkyl of 3 to 7 carbon atoms or cycloalkenyl of 3 to 7 carbon atoms, aryl, especially phenyl, unsubstituted or substituted by 1 to 3 of the same or different substituents selected from the group consisting of alkyl, especially lower alkyl, alkoxy, especially lower alkoxy, halogen, nitro, cyano, trifluoromethyl, carbalkoxy, especially carb.lower alkoxy and $SO_n$—alkyl, especially lower alkyl wherein $n$ is 0, 1 or 2, or $R^2$ is naphthyl, quinolyl, isoquinolyl, pyridyl, pyrimidyl, thenyl, furyl or pyrryl unsubstituted or substituted by 1 or more, preferably 1 or 2, substituents selected from the group consisting of alkyl, especially lower alkyl, alkoxy, especially lower alkoxy and halogen; and $R^3$ is a straight or branched chain hydrocarbon, especially lower alkyl, lower alkenyl or lower alkynyl or said hydrocarbon interrupted by 1 or 2 oxygen atoms, especially lower alkyl, lower alkenyl or lower alkynyl interrupted by 1 or 2 oxygen atoms.

According to the present invention, the 3,4-dihydropyridones of formula I are produced by reacting an α,β-unsaturated carboxylic acid ester of the formula

(II)

wherein R is alkyl, preferably of 1 to 6 carbon atoms and especially of 1 to 4 carbon atoms, alkenyl of 2 to 6 carbon atoms or alkynyl of 2 to 6 carbon atoms, and $R^1$ and $R^2$ are as above defined, with an amidine of the formula

(III)

wherein $R^3$ is as above defined, and recovering the compound produced.

It is distinctly surprising that according to the reaction of the invention the new compounds are produced in such good yields and in such high purity since from the prior art, one would have expected an addition of the amidine radical to the α,β-unsaturated carbonyl radical to give a dihydropyrimidone IV, in accordance with the following equation:

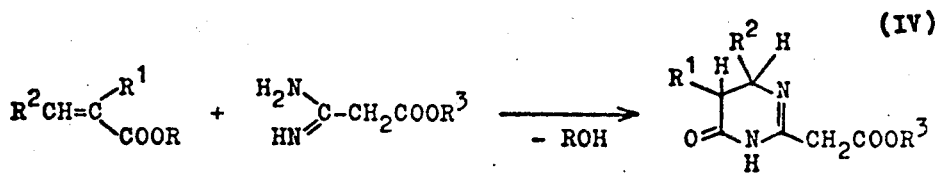
(IV)

(compare E. F. Silversmith, J. Org. Chem, 27, 4090 (1962)).

An important advantage of the process according to the invention is that it can give high yields and products of high purity and that it can be carried out as a one-step process with little technical effort, and highly economically.

If, for example, 3-nitrobenzylidenemalonic acid diethyl ester and amidinoacetic acid ethyl ester are employed as the starting components, the course of the process of the invention can be illustrated by the following equation:

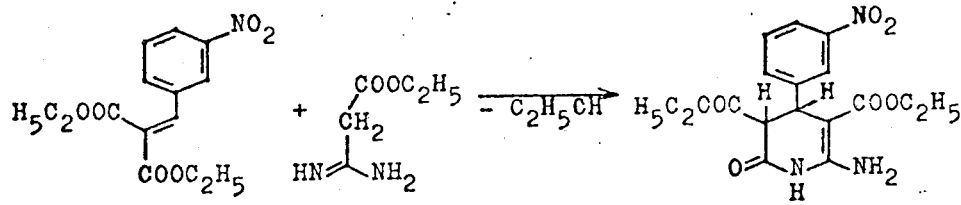

The compounds of the present invention are particularly useful because of their long-lasting coronary dilating action, thereby being useful vasodilators, and also because of their anti-hypertensive activity.

According to one embodiment of the present invention, $R^1$ is hydrogen, straight or branched chain alkyl of 1 to 4 carbon atoms or —COOR' wherein R' is straight or branched chain alkyl of 1 to 4 carbon atoms, straight or branched chain alkenyl of 2 to 4 carbon atoms, straight or branched chain alkynyl of 2 to 4 carbon atoms, cycloalkyl of 3 or 4 carbon atoms, cycloalkenyl of 3 to 4 carbon atoms or straight or branched chain alkyl of 1 to 4 carbon atoms, straight or branched chain alkenyl of 2 to 4 carbon atoms, straight or branched chain alkynyl of 2 to 4 carbon atoms, cycloalkyl of 3 or 4 carbon atoms or cycloalkenyl of 3 or 4 carbon atoms interrupted by 1 oxygen atom; $R^2$ is straight or branched chain alkyl of 1 to 6 carbon atoms, straight or branched chain alkenyl of 2 to 6 carbon atoms, straight or branched chain alkynyl of 2 to 6 carbon atoms, cycloalkyl of 3 to 6 carbon atoms, cycloalkenyl of 3 to 6 carbon atoms, phenyl substituted by 1 or 2 of the same or different substituents selected from the group consisting of alkyl of 1 to 4 carbon atoms, alkoxy of 1 to 4 carbon atoms, halogen (especially chloro or bromo), nitro, cyano, trifluoromethyl, carbalkoxy of 1 to 4 carbon atoms in the alkoxy moiety and $SO_n$—alkyl of 1 to 4 carbon atoms wherein $n$ is 0 or 2, or $R^2$ is naphthyl, quinolyl, pyridyl, thenyl or furyl unsubstituted or substituted by 1 or 2 substituents selected from the group consisting of alkyl of 1 to 4 carbon atoms, alkoxy of 1 to 4 carbon atoms and halogen (especially chloro or bromo); and $R^3$ is lower alkyl or lower alkenyl.

According to another embodiment of the present invention, $R^1$ is hydrogen, straight or branched chain alkyl of 1 to 4 carbon atoms or —COOR' wherein R' is straight or branched chain alkyl of 1 to 4 carbon atoms or straight or branched chain alkenyl of 2 to 4 carbon atoms; $R^2$ is phenyl unsubstituted or substituted by 1 or 2 substituents selected from the group consisting of alkyl of 1 to 4 carbon atoms, alkoxy of 1 to 4 carbon atoms, chloro, bromo, nitro, cyano, trifluoromethyl and S—alkyl of 1 to 4 carbon atoms, or $R^2$ is naphthyl, thenyl, furyl or pyridyl; and $R^3$ is straight or branched chain alkyl of 1 to 4 carbon atoms.

According to another embodiment of the present invention, $R^1$ is hydrogen or —COOR' wherein R' is alkyl of 1 to 3 carbon atoms or alkenyl of 2 or 3 carbon atoms; $R^2$ is phenyl; phenyl substituted by chloro, dichloro, methyl, methoxy, nitro, trifluoromethyl or thiomethyl; naphthyl, thenyl; or furyl; and $R^3$ is alkyl of 1 to 3 carbon atoms.

The $\alpha,\beta$-unsaturated carboxylic acid esters of formula II used according to the invention are already known or can be produced by known methods (Org. Reactions XV, 204 and thereafter (1967)).

Representative $\alpha,\beta$-unsaturated carboxylic esters include:

Crotonic acid ethyl ester,
$\gamma,\gamma$-dimethylcrotonic acid ethyl ester,
cinnamic acid ethyl ester,
2'-methoxycinnamic acid ethyl ester,
3'-nitrocinnamic acid ethyl ester,
4'-chlorocinnamic acid ethyl ester,
2'-trifluoromethylcinnamic acid ethyl ester,
2'-cyanocinnamic acid methyl ester,
benzylidenemalonic acid diethyl ester,
ethylidenemalonic acid diethyl ester,
isopropylidenemalonic acid dimethyl ester,
$\Delta^3$-cyclohexenylidenemalonic acid diethyl ester,
2'-nitrobenzylidenemalonic acid dimethyl ester,
2'-chlorobenzylidenemalonic acid diallyl ester,
2'-methoxybenzylidenemalonic acid dipropargyl ester,
2'-trifluoromethylbenzylidenemalonic acid diisopropyl ester,
3'-nitrobenzylidenemalonic acid diethyl ester,
2-methylsulphonylbenzlidenemalonic acid dimethyl ester,
2-methylmercaptobenzylidenemalonic acid diethyl ester,
2'-methylbenzylidenemalonic acid diallyl ester,
3'-methylbenzylidenemalonic acid dicyclohexyl ester,
2'-cyanobenzylidenemalonic acid diethyl ester,
3'-nitro-6'-chlorobenzylidenemalonic acid diethyl ester,
2',6'-dichlorobenzylidenemalonic acid dimethyl ester,
3',4',5'-trimethoxybenzylidenemalonic acid diethyl ester,
(1'-naphthylidene)-malonic acid diethyl ester,
(2'-naphthylidene)-malonic acid diethyl ester,
(2'-methoxy-1'-naphthylidene)-malonic acid diethyl ester,
(4'-bromo-1'-naphthylidene)-malonic acid diisopropyl ester,
(2'-quinolyl)-methylidenemalonic acid diethyl ester,
(3'-quinolyl)-methylidenemalonic acid diethyl ester,
(1'-isoquinolyl)-methylidenemalonic acid diethyl ester,
$\alpha$-pyridylmethylidenemalonic acid diethyl ester,
$\alpha$-pyridylmethylidenemalonic acid diallyl ester,
$\beta$-pyridylmethylidenemalonic acid dimethyl ester,
$\gamma$-pyridylmethylidenemalonic acid diethyl ester,
(4',6'-dimethoxy-5'-pyrimidyl)-methylidenemalonic acid diethyl ester,
(2'-thenyl)-methylidenemalonic acid diethyl ester,
2'-furfurylidenemalonic acid diallyl ester,
(2'-pyrryl)-methylidenemalonic acid diethyl ester and
3'-carbethoxybenzylidenemalonic acid dimethyl ester.

The amidines of formula III which can be used in the process according to the invention are already known or can be produced by known processes (S. M. McElvain, B. E. Tate, J.A.C.S. 73, 2760 (1951)).

Representative amidines include

Amidinoacetic acid methyl ester,
amidinoacetic acid ethyl ester,
amidinoacetic acid n-propyl ester,
amidinocetic acid isopropyl ester,
amidinoacetic acid propargyl ester,
amidinoacetic acid butyl ester,
amidinoacetic acid $\beta$-methoxy-ethyl ester and
amidinoacetic acid ($\alpha$- and $\beta$-)-ethoxyethyl esters.

The amidines can be employed either in the free form or in the form of their salts (for example hydrohalides). They can be liberated from the salts by means of basic reagents (for example alkali alcoholates).

The reaction in the process of the invention is preferably carried out in an inert organic solvent at a temperature of from about 20°C to about 200°C preferably at the boiling point of the solvent using substantially equimolar proportions of the reagents.

Any inert organic solvent may be used. Preferably solvents include alcohols (such as methanol, ethanol and propanol), ethers (such as dioxane and diethyl ether), glacial acetic acid, pyridine, dimethylformamide, dimethylsulphoxide and acetonitrile.

The reaction can be carried out under normal pressure but also under elevated pressure. In general, normal pressure is used.

The following types of activity have been demonstrated in in vivo animal experiments:

1. On parenteral, oral and perlingual administration the compounds of the present invention produce a distinct and long-lasting dilation of the coronary vessels. This action on the coronary vessels is intensified by a simultaneous nitrile-like effect of reducing the load on the heart. The compounds influence or modify the heart metabolism in the sense of an energy saving.

2. The compounds of the present invention lower the blood pressure of normotonic and hypertonic animals and can thus be used as anti-hypertensive agents.

3. The excitability of the stimulus formation and excitation conduction system within the heart is lowered, so that an anti-fibrillation action demonstrable at therapeutic doses results.

4. The tone of the smooth muscle of the vessels is greatly reduced under the action of the compounds. This vascular-spasmolytic action can take place in the entire vascular system or can manifest itself more or less isolated in circumscribed vascular regions (such as, for example, the central nervous system).

5. The compounds of the present invention have strongly muscular-spasmolytic actions which manifest themselves on the smooth muscle of the stomach, the intestinal tract, the urogenital tract and the respiratory system.

6. The compounds of the present invention influence the cholesterol level and lipid level of the blood.

The present invention includes pharmaceutical compositions embodying a compound of the present invention as the active ingredient. The pharmaceutical compositions of the present invention contain a major or minor amount, e.g. from 99.5 to 0.1%, preferably 90% to 0.5%, of the active agent as herein defined in combination with a pharmaceutical carrier, the carrier comprising one or more solid, semi-solid or liquid diluent, filler and formulation adjuvant which is non-toxic, inert and pharmaceutically acceptable. Such pharmaceutical compositions are preferably in dosage unit form; i.e. physically discrete units containing a predetermined amount of the drug corresponding to a fraction or multiple of the dose which is calculated to produce the desired therapeutic response. The dosage units can contain one, two, three, four or more single doses or, alternatively, one-half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage for I.V. administration will be from 2.5 mg to 1.8 g, preferably 5 mg to 900 mg. The preferred oral administration is 25 mg to 9 g, preferably 50 mg to 4.5 g. In each case, the dosage represents the amount of active ingredients to be administered. The daily dosage on I.V. administration is preferably 0.5 to 20 mg/kg. In some instances a sufficient therapeutic effect can be obtained at a lower dose while in others, a larger dose will be required.

Oral administration can be effected utilizing solid and liquid dosagge unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitably comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The medicaments can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low melting water soluble or insoluble solids such as polyethylene glycol, cocoa butter, higher esters as for example myristyl palmitate, or mixtures thereof.

Topical administration can be effected utilizing solid dosage unit forms such as powders or liquid or semiliquid dosage unit forms such as solutions, suspensions, ointments, pastes, creams and gels. The powders are formulated utilizing such carriers as talc, bentonite, silicic acid, polyamide powder and the like. Liquid and semiliquid formulations can utilize such carriers, in addition to those described above, as polyethylene glycol, vegetable and mineral oils, alcohols such as isopropanol and the like. Other excipients such as emulsifiers, preservatives, colorants, perfumes and the like can also be present. Formulations can also be administered as an aerosol, utilizing the usual propellants such as the chlorofluorohydrocarbons. Oral and I.V. compositions are preferred.

The coronary action of compounds representative of those of the present invention is shown in Table I:

Table I

| Compound of: | Distinctly discernible rise in the oxygen saturation in the coronary sinus |
| --- | --- |
| Example 2 | 5 mg/kg i.v. |
| Example 7 | 5 mg/kg i.v. |
| Example 12 | 5 mg/kg i.v. |

The coronary action was ascertained on narcotised heartcatheterised mongrel dogs by measuring the rise in oxygen saturation in the coronary sinus after intravenous administration.

The blood pressure lowering effect of compounds of the present invention is shown in Table II. This effect is indicative of anti-hypertensive activity. The dose indicated in the second column is that required to cause a blood pessure lowering of at least 15 mm Hg.

Table II

| Compound of: | Blood pressure lowering in high blood pressure rats, mg/kg administered orally. |
| --- | --- |
| Example 3 | from 0.3 |
| Example 12 | from 3.0 |

The following non-limitative examples more particularly point out and define the present invention:

EXAMPLE 1

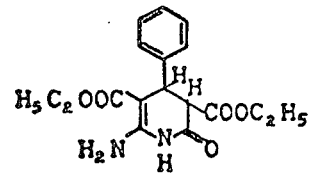

Heating a solution of 12.4 g of benzylidenemalonic acid diethyl ester and 6.5 g of amidinoacetic acid ethyl ester in 100 ml of ethanol for 4 hours yielded 4-phenyl-6-amino-3,4-dihydropyrid-2-one-3,5-dicarboxylic acid diethyl ester of melting point 218°C (ethanol). Yield 76% of theory.

EXAMPLE 2

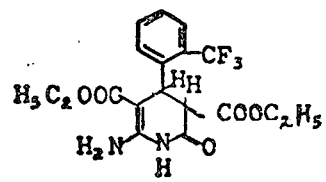

Boiling a solution of 15.8 g of 2'-trifluoromethylbenzylidenemalonic acid diethyl ester and 6.5 g of amidinoacetic acid ethyl ester for 5 hours yielded 4-(2'-trifluoromethylphenyl)-6-amino-3,4-dihydropyrid-2-one-3,5-dicarboxylic acid diethyl ester of melting point 164°C (ethanol). Yield 62% of theory.

EXAMPLE 3

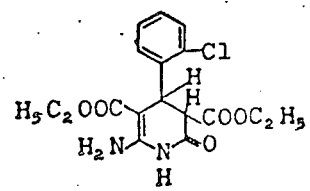

Boiling a solution of 14.1 g of 2'-chlorobenzylidenemalonic acid diethyl ester and 6.5 g of amidinoacetic acid ethyl ester in 100 ml of ethanol for 4 hours yielded 4-(2'-chlorophenyl)-6-amino-3,4-dihydropyrid-2-one-3,5-dicarboxylic acid diethyl ester of melting point 190°C (ethanol). Yield 69% of theory.

EXAMPLE 4

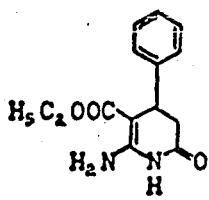

Boiling a solution of 8.8 g of cinnamic acid ethyl ester and 6.5 g of amidinoacetic acid ethyl ester in 80 ml of ethanol for 4 hours yielded 4-phenyl-6-amino-3,4-dihydropyrid-2-one-5-carboxylic acid ethyl ester of melting point 181°C (ethanol). Yield 49% of theory.

EXAMPLE 5

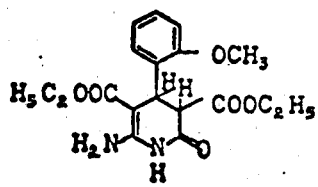

Heating a solution of 13.9 g of 2'-methoxybenzylidenemalonic acid diethyl ester and 6.5 g of amidinoacetic acid ethyl ester in 100 nl of ethanol for 4 hours yielded 4-(2'-methoxyphenyl)-6-amino-3,4-dihydropyrid-2-one-3,5-dicarboxylic acid diethyl ester of melting point 198°C (ethanol). Yield 55% of theory.

EXAMPLE 6

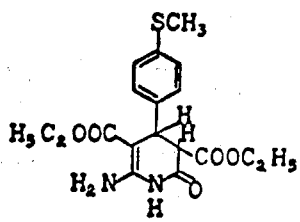

Boiling a solution of 15.4 g of 4'-methylmercaptobenzylidenemalonic acid diethyl ester and 6.5 g of amidinoacetic acid ethyl ester in 100 ml of ethanol for 4 hours yielded 4-(4'-methylmercaptophenyl)-6-amino-3,4-dihydropyrid-2-one-3,5-dicarboxylic acid diethyl ester of melting point 168°C (ethanol).

EXAMPLE 7

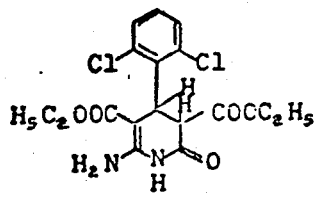

Boiling a solution of 15.9 g of 2',6'-dichlorobenzylidenemalonic acid diethyl ester and 6.5 g of amidinoacetic acid ethyl ester in 120 ml of ethanol for 4 hours yielded 4-(2',6'-dichlorophenyl)-6-amino-3,4-dihydropyrid-2-one-3,5-dicarboxylic acid diethyl ester of melting point 245° (ethanol/dimethylformamide). Yield 78% of theory.

EXAMPLE 8

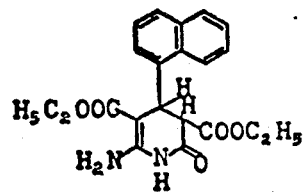

Heating 14.9 g of 1'-naphthylidenemalonic acid diethyl ester and 6.5 g of amidinoacetic acid ethyl ester in 100 ml of ethanol for 4 hours yielded 4-(1'-naphthyl)-6-amino-3,4-dihydropyrid-2-one-3,5-dicarboxylic acid diethyl ester of melting point 206°C (alcohol). Yield 66% of theory.

EXAMPLE 9

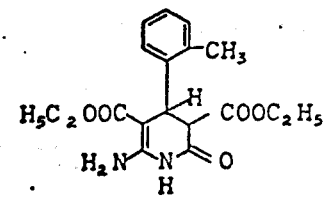

Boiling a solution of 13.1 g of 2'-methylbenzylidenemalonic acid diethyl ester and 6.5 g of amidinoacetic acid ethyl ester in 100 ml of ethanol for 8 hours yielded 4-(2'-methylphenyl)-6-amino-3,4-dihydropyrid-2-one-3,5-dicarboxylic acid diethyl ester of melting point 176°C (ethanol). Yield 80% of theory.

EXAMPLE 10

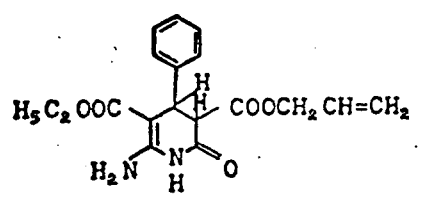

Heating a solution of 13.0 g of benzylidenemalonic acid diallyl ester and 6.5 g of amidinoacetic acid ethyl ester in 100 ml of ethanol for 4 hours yielded 4-phenyl-6-amino-3,4-dihydropyrid-2-one-3,5-dicarboxylic acid 3-allyl ester-5-ethyl ester of melting point 156°C (ethanol). Yield 59% of theory.

EXAMPLE 11

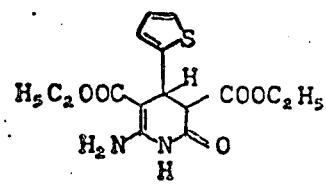

Boiling a solution of 12.8 g of (2'-thenyl)-methylidenemalonic acid diethyl ester and 6.5 g of amidinoacetic acid ethyl ester in 100 ml of ethanol for 4 hours yielded 4-(2'-thenyl)-6-amino-3,4-dihydropyrid-2-one-3,5-dicarboxylic acid diethyl ester of melting point 193°C (ethanol). Yield 57% of theory.

EXAMPLE 12

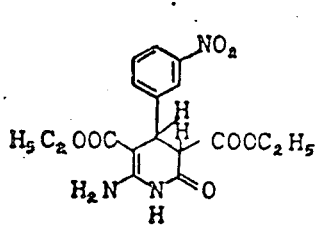

Heating a solution of 14.7 g of 3'-nitrobenzylidenemalonic acid diethyl ester and 6.5 g of amidinoacetic acid ethyl ester in 100 ml of ethanol for 4 hours yielded 4-(3'-nitrophenyl)-6-amino-3,4-dihydropyrid-2-one-3,5-dicarboxylic acid diethyl ester of melting point 197°C (ethanol). Yield 82% of theory.

EXAMPLE 13

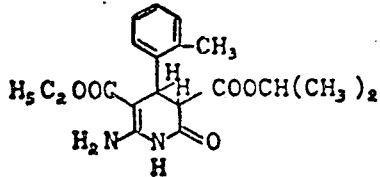

Boiling a solution of 14.5 g of 2'-methylbenzylidenemalonic acid diisopropyl ester and 6.5 of ammidinoacetic acid ethyl ester in 100 ml of ethanol for 4 hours yielded 4-(2'-methylphenyl)-6-amino-3,4-dihydropyrid-2-one-3,5-dicarboxylic acid 3-isopropyl ester-5-ethyl ester of melting point 175°C (isopropanol). Yield 54% of theory.

EXAMPLE 14

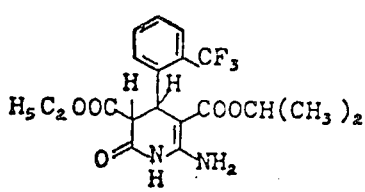

heating a solution of 15.8 g of 2'-trifluoromethylbenzylidenemalonic acid diethyl ester and 7.2 g of amidinoacetic acid isopropyl ester in 100 ml of ethanol for 4 hours yielded 4-(2'-trifluoromethylphenyl)-6-amino-3,4-dihydropyrid-2-one-3,5-dicarboxylic acid 3-ethyl ester-5-isopropyl ester of melting point 169°C (isopropanol). Yield 62% of theory.

EXAMPLE 15

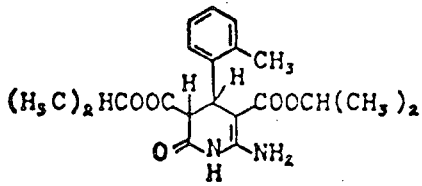

Boiling a solution of 14.5 g of 2'-methylbenzylidenemalonic acid diisopropyl ester and 7.2 g of amidinoacetic acid isopropyl ester in 150 ml of isopropanol for 5 hours yielded 4-(2'-methylphenyl)-6-amino-3,4-dihydropyrid-2-one-3,5-dicarboxylic acid diisopropyl ester of melting point 165°C (isopropanol). Yield 66% of theory.

EXAMPLE 16

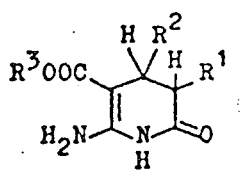

Heating a solution of 11.9 g of (2'-furfurylidene)malonic acid diethyl ester and 6.5 g of amidinoacetic acid diethyl ester in 150 ml of ethanol for 4 hours yielded 4-(2'-furyl)-6-amino-3,4-dihydropyrid-2-one-3,5-dicarboxylic acid diethyl ester of melting point 170°C (ethanol). Yield: 44% of theory.

What is claimed is:
1. A process for the production of a compound of the formula:

$$\text{structure}$$

wherein $R^1$ is hydrogen or straight or branched chain lower alkyl; $R^2$ is lower alkyl, lower alkenyl, lower alkynyl, cycloalkyl of 3 to 7 carbon atoms, cycloalkenyl of 3 to 7 carbon atoms, aryl unsubstituted or substituted by 1 to 3 of the same or different substituents selected from the group consisting of lower alkyl, lower alkoxy, halogen, nitro, cyano, trifluoromethyl, carb. lower alkoxy and $SO_n$-lower alkyl wherein $n$ is 0, 1 or 2, or $R^2$ is naphthyl, quinolyl, isoquinolyl, pyridyl, pyrimidyl, thenyl, suryl or pyrryl unsubstituted or substituted by 1 or 2 substituents selected from the group consisting of lower alkyl, lower alkoxy and halogen; and $R^3$ is straight or branched chain lower alkyl, straight or branched chain lower alkenyl, straight or branched chain lower alkynyl, or straight or branched chain lower alkyl, straight or branched chain lower alkenyl or straight or branched chain lower alkynyl interrupted by 1 or 2 oxygen atoms;

which comprises reacting an α,β-unsaturated carboxylic acid ester of the formula

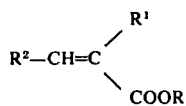

wherein R is alkyl of 1 to 6 carbon atoms, alkenyl of 2 to 6 carbon atoms or alkynyl of 2 to 6 carbon atoms; and $R^1$ and $R^2$ are as above defined, with an amidine of the formula:

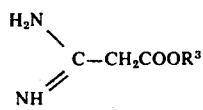

wherein $R^3$ is as above defined, and recovering the compound produced.

2. A process according to claim 1 wherein R is alkyl of 1 to 4 carbon atoms; $R^1$ is hydrogen or straight or branched chain alkyl of 1 to 4 carbon atoms; $R^2$ is straight or branched chain alkyl of 1 to 6 carbon atoms, straight or branched chain alkenyl of 2 to 6 carbon atoms, straight or branched chain alkynyl of 2 to 6 cycloalkyl of 3 to 6 carbon atoms, cycloalkenyl of 3 to 6 carbon atoms, phenyl substituted by 1 or 2 of the same or different substituents selected from the group consisting of alkyl of 1 to 4 carbon atoms, alkoxy of 1 to 4 carbon atoms, halogen, nitro, cyano, trifluoromethyl, carb.alkoxy of 1 to 4 carbon atoms in the alkoxy moiety and $SO_n$-alkyl of 1 to 4 carbon atoms wherein n is 0 or 2, or $R^2$ is naphthyl, quinolyl, pyridyl, thenyl or furyl unsubstituted or substituted by 1 or 2 substituents selected from the group consisting of alkyl of 1 to 4 carbon atoms, alkoxy of 1 to 4 carbon atoms and halogen; and $R^3$ is lower alkyl or lower alkenyl.

3. A process according to claim 1 wherein R is alkyl of 1 to 4 carbon atoms; $R^1$ is hydrogen or straight or branched chain alkyl of 1 to 4 carbon atoms; $R^2$ is phenyl unsubstituted or substituted by 1 or 2 substituents selected from the group consisting of alkyl of 1 to 4 carbon atoms, alkoxy of 1 to 4 carbon atoms, chloro, bromo, nitro, cyano, trifluoromethyl and S-alkyl of 1 to 4 carbon atoms, or $R^2$ is naphthyl, thenyl, furyl or pyridyl; and $R^3$ is straight or branched chain alkyl of 1 to 4 carbon atoms.

4. A process according to claim 1 wherein R is alkyl of 1 to 4 carbon atoms; $R^1$ is hydrogen; $R^2$ is phenyl; phenyl substituted by chloro, dichloro, methyl, methoxy, nitro, trifluoromethyl or thiomethyl; naphthyl; thenyl; or furyl; and $R^3$ is alkyl of 1 to 3 carbon atoms.

5. A process according to claim 1 wherein the reaction is carried out in an inert organic solvent at a temperature from about 20°C to about 200°C.

6. A process for the production of a compound of the formula

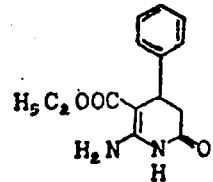

which comprises reacting cinnamic acid ethyl ester and amidonoacetic acid ethyl ester, and recovering the compound produced.

* * * * *